United States Patent [19]
Abbas et al.

[11] Patent Number: 5,856,283
[45] Date of Patent: Jan. 5, 1999

[54] COMPOSITION

[75] Inventors: Syed Husain Abbas, Belle Mead; Ben Gu, East Brunswich; AnBen Hwang, Verona; Ravi Subramanyam, Belle Mead, all of N.J.

[73] Assignee: Colgate-Palmolive Co., New York, N.Y.

[21] Appl. No.: 911,204

[22] Filed: Aug. 14, 1997

[51] Int. Cl.$^6$ .................................. C11D 1/06; C11D 3/48
[52] U.S. Cl. .................... 510/131; 510/133; 510/141; 510/152; 510/155; 510/388; 510/479
[58] Field of Search ...................... 510/131, 133, 510/141, 152, 153, 155, 156, 488, 479, 388

[56] References Cited

U.S. PATENT DOCUMENTS

| | | |
|---|---|---|
| 5,233,087 | 8/1993 | Cripe . |
| 5,296,159 | 3/1994 | Wilson et al. ........................ 252/117 |

FOREIGN PATENT DOCUMENTS

| | | | |
|---|---|---|---|
| 0 311 343 A2 | 12/1989 | European Pat. Off. ........ C11D 10/04 |
| 2175799 | 6/1990 | Japan . | |
| 04074102A | 3/1992 | Japan ............................... C11D 3/48 |
| 8113529 | 7/1996 | Japan . | |

*Primary Examiner*—Paul Lieberman
*Assistant Examiner*—Gregory E. Webb
*Attorney, Agent, or Firm*—Martin B. Barancik

[57] ABSTRACT

A solid composition comprising
  a. a cleansing effective amount of an anionic surfactant or mixture thereof,
  b. an alcohol ethoxycarboxylic acid of the formula $$R-(OCH_2CH_2)_n-O\ CH_2COOH$$

wherein R is an alkyl of an average of about 8 to 20 carbon atoms inclusive and n is a number of 1 to about 20,
  c. a carbanilide antibacterial agent in antibacterial effective quantities wherein component b is in sufficient quantities to solubilize the carbanilide antibacterial agent.

6 Claims, No Drawings

COMPOSITION

BACKGROUND OF THE INVENTION

Antibacterial agents have been placed into cleansing compositions for many years. However, not all antibacterial agents are active or present stable entities in specific cleansing compositions. Some antibacterial agents are easier to stabilize and maintain their activity in solid compositions. Other antibacterial agents more readily maintain activity and stability in liquid cleansing compositions. Antibacterial agents of the carbanilide family are well known to be difficult to solubilize and also to stabilize in liquid systems, particularly aqueous liquid systems and even in solids such as bars. The most well known of these carbanilide antibacterial agents is triclocarban.

A new method of solubilizing carbanilide antibacterial effective amounts and utilizing them in a solid cleansing composition has been discovered. The antibacterial active agent is solubilized in an alcohol ethoxycarboxylate. The solubilized carbanilide agent is then incorporated into a solid cleansing composition by standard methods. The cleansing composition having the alcohol ethoxycarboxyl acid also is superfatted by the alcohol ethoxycarboxyl acid. Additionally, the alcohol ethoxycarboxyl acid seems to provide an additional benefit of improving the rinsability of the cleansing compositions from skin.

SUMMARY OF THE INVENTION

In accordance with the invention there is a solid composition comprising a) a cleansing effective amount of an anionic surfactant or mixture thereof, b) an alcohol ethoxycarboxylic acid of the formula R—(OCH$_2$CH$_2$)$_n$—O—CH$_2$—COOH wherein R is an alkyl of an average of about 8 to 20 carbon atoms inclusive and n is a number of 1 to about 20, c) a carbanilide antibacterial agent in antibacterial effective quantities wherein component b is present in sufficient quantities to solubilize the carbanilide antibacterial agent.

A further aspect of the invention is the presence of component b in quantities sufficient to superfat the solid composition.

A still further aspect of the invention is the presence of component b in quantities sufficient to provide easier rinsing of the cleansing composition from the cleansed surface.

An additional aspect of the invention is the solubilized composition of carbanilide antibacterial agent in an alcohol ethoxycarboxylic acid.

DETAILED DESCRIPTION OF THE INVENTION

Any anionic surfactant can be employed. Examples of such anionic surfactants include soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols (C$_8$–C$_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; or direct esterification of sodium isethionate with fatty acid water soluble salts of condensation products of fatty acids with sarcosine; and others known in the art, for example taurate, phosphates, and any mixtures thereof.

Although not necessary other surfactants may be present in the composition. Examples of these surfactants include zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxylate, sulfonate, sulfate, phosphate, or phosphonate. A general formula for these compounds is:

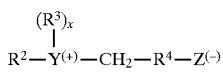

wherein R$^2$ contains an alkyl, alkenyl, or hydroxy alkyl radical of from about 8 to about 18 carbon atoms, from 0 to about 10 ethylene oxide moieties and from 0 to 1 glyceryl moiety;

Y is selected from the group consisting of nitrogen, phosphorus, and sulfur atoms; R3 is an alkyl or monohydroxyalkyl group containing 1 to about 3 carbon atoms; X is 1 when Y is a 20 sulfur atom and 2 when Y is a nitrogen or phosphorus atom, R$^4$ is an alkylene or hydroxyalkylene of from 0 to about 4 carbon atoms and Z is a radical selected from the group consisting of carboxylate, sulfonate, sulfate, phosphonate, and phosphate group.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphos-phonio)-propane-1-phosphonate; and 5-[N,N-di(3-hydroxypropyl)-N-hexadecylam-monio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., "carboxylate, sulfonate, sulfate, phosphate, or phosphonate." Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see *CTFA Cosmetic Ingredient Dictionary,* 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

Generally there should be at least 5 wt. % of an anionic surfactant or mixture thereof present in the solid cleansing composition. The total amount of surfactant should not be above about 88 wt. % of the composition.

Present in the composition should be a carbanilide antibacterial agent in an effective amount to bring about antibacterial action. Examples of the carbanilide antibacterial family include various diphenylanilides preferably having halo substituent(s) on the ring, see Colwell, U.S. Pat. No. 5,496,555. Particularly preferred is the antibacterial carbanilide well known as triclocarban, CAS #101-20-2. Triclocarban is also known as n-(4-chlorophenyl)-n (3,4-dichlorophenyl) urea. Its more trivial name is 3,4,4-trichlorocarbanilide and is abbreviated as triclocarban or TCC.

It has now been found that these antibacterial agents, particularly triclocarban, can be effectively solubilized and stabilized in solid cleansing composition through the use of a compound of the structure R—(OCH$_2$ CH$_2$)$_n$—O—CH$_2$ COOH wherein R is an alkyl of an average of about 8 to 20 carbon atoms inclusive and n is a number of 1 to about 20. Preferably R is alkyl of about 10 to 18 carbon atoms and n is a number of about 3 to about 12. The quantity of long chain ethoxylated carboxy acids (AEC) needed to solubilize the carbanilide antibacterial agent, preferably TCC, is relatively small. For example at room temperature (25° C.) the amount of AEC necessary to solubilize the carbanilides, preferably TCC, is about 5 times the amount of antibacterial agent, preferably 6 or 7 times the amount of antibacterial agent, preferably TCC. At elevated temperatures, less AEC is needed for example about 3 to about 4 times the amount of TCC. The maximum amount of AEC is not unduly significant but is somewhat dependent upon for example cost and final properties of the solid cleansing composition. Generally no more than about 15 times the amount of TCC is generally employed. When used in a solid cleansing composition, the amount of carbanilide antibacterial agents, preferably TCC, is about 0.1 to about 1.5 wt. % of the cleansing composition, preferably about 0.15 to about 1.0 wt. %. When used in a solid cleansing composition, the quantity of AEC is about 0.5 to about 20, preferably about 2 to about 7 wt. % of the solid cleansing composition. This amount of AEC when used in the solid cleansing composition is sufficient to maintain its solubilization of the carbanilides, preferably TCC in the solid composition so that it is evenly dispersed throughout the solid composition, that is, there is a minimum of high density (clumping) and low densities of TCC throughout the solid cleansing composition.

With respect to the solid cleansing composition, it is preferred to have at least some soap therein for the purposes of providing lather and structure to the solid cleansing composition, preferably in bar shape. At least 5 wt. % of the solid cleansing composition should be soap. Generally no more than about 88 wt. % of the solid cleansing composition should be soap. Various minimum of soap can be used such as 10, 20 or 30 wt. % of the cleansing composition. The maximum can be 80, 70, 70, 60, 50 or 40 wt. %. Generally, the lower amount of soap in the solid cleansing composition, the higher the content of synthetic surfactants. Also present in the cleansing composition can be superfatting agents such as citric acid and particularly the long chain alkyl carboxylic acids such as lauric, myristic, palmitic and stearic. The ethoxylated carboxylic acids (AEC) which solubilize the carbanilide antibacterial agent also function as an effective superfatting agent as well. It has also been found that AEC provide effective rinsing properties as well, even when the carbanilide antibacterial agent is present.

Other agents can also be present in the solid cleansing composition as well including one or more of emollients, coloring agents, fragrances, preservatives, ultraviolet protecting agents and the like. Moisture is also present in the composition and is anywhere from about 5 to about 15 wt. % of the solid cleansing components although higher or lower quantities can be employed.

Below are examples illustrating the beneficial properties of this disclosed invention. These examples are intended to illustrate the breadth of the invention and not unduly limit the broad inventive concept.

EXAMPLE 1

The effectiveness of utilizing AEC for solubilizing carbanilide antibacterial agents, particularly TCC, is demonstrated by the data below. In the table below the "Neodoxes" employed are primary alkyl ethoxylated carboxylic acids of the formula earlier in the specification

TABLE 1

| AEC Name | R | n |
|---|---|---|
| Neodox 23-11 | 12–13 | 11 |
| Neodox 23-4 | 12–13 | 4 |
| Neodox 1-4 | 11 | 4 |
| Neodox 45-7 | 14–15 | 7 |

The data shown in the Table below at 25° C. is obtained by adding TCC to the particular AEC until cloudiness as observed visually occurs. The data at elevated temperatures is obtained by starting with a fixed amount of TCC which is not soluble in the AEC being evaluated and gradually raising the temperature of the system until it becomes clear as observed visually. Below are the results:

TABLE 2

| AEC Name | Solubility - Temp °C./TCC wt. % | | |
|---|---|---|---|
| Neodox 23-11 | 25° C./12.7% | 86° C./15.0% | 123° C./20.0% |
| Neodox 23-4 | 25° C./12.0% | 65° C./15.0% | 93° C./20.0% |
| Neodox 1-4 | 28° C./11.4% | — | 96° C./20.0% |
| Neodox 45-7 | — | 71° C./15.0% | 111° C./20.0% |

EXAMPLE 2

Wool Binding Test

Accurately weighed (about 90 mg) swatches of wool fabric are immersed in 10 ml of soap solution with 300 ppm hardness and containing radiolabelled [C- 14] fatty acids. The solutions are incubated at 50° C. for 24 hours. After filtration, the dry swatches are soaked in 10 ml of 300 ppm hard water and incubated at 50° C. for another 24 hours. The swatches are filtered and digested in 1 ml of 2N sodium hydroxide solution at 80° C. for one hour. The cold digested solution is neutralized with 0.2 ml concentrated perchloric acid and diluted with 10 ml Ecolume. The amount of radioactive soap bound to the wool fabric is determined by scintillation counting.

Calculation:

$$\frac{F \times 0.05 \times A \times 10^6}{S \times MW \times W_{W\text{-}F}}$$

F—scintillation counting of wool fabric;
S—scintillation counting of 1 ml 5% soap solution;
WW-F—weight of wool fabric;
A—percent of fatty material, corresponding to radiolabelled fatty acid;
MW—molecular weight of the fatty material.

The soap employed is obtained from 60 wt. % tallow and 40 wt. % coconut oil with about 12 wt. % moisture. To this is added 7 wt. % of the tested materials. The assay is a recognized in vitro assay to evaluate the level of soap binding to keratinous materials such as skin. "A" as used below is the soap as described above.

TABLE 3

| Formula (5% Solution) | Palmintate $C^{14}$ Residue $\mu$ mole/g wool ($\mu$ mol/g) |
|---|---|
| 7% Lauric acid/ A | 128.0 ± 1.6 |
| 7% Neodox 23-4/ A | 70.9 ± 2.3 |
| 7% Neodox 23-11/ A | 69.5 ± 1.1 |
| A | 128.8 ± 3.9 |

The data shows that the usage of AECs reduce the soap binding to skin in comparison to nonethoxylated fatty acid. Soap binding to skin is associated with skin tightness and dryness.

EXAMPLE 3

The same experimental methodology was used in Example 3 as Example 2. However, soap A had 11.8 wt. % moisture. Soap B has 0.5 wt. % TCC but otherwise is the same composition as soap A. Below are the results.

| Formula (5% Solution) | Palmitate $C^{14}$ residue $\mu$ mole/g wool |
|---|---|
| 7% Lauric acid/ A | 78.0 +/− 2.4 |
| 7% Neodox 23-4/ A | 44.9 +/− 1.7 |
| 7% Neodox 23-11/ A | 44.0 +/− 1.5 |
| A | 78.4 +/− 2.9 |
| 7% Lauric acid/ B | 76.0 +/− 2.1 |
| 7% Neodox 23-4/ B | 45.1 +/− 1.3 |
| 7% Neodox 23-11/ B | 43.7 +/− 1.9 |
| B | 79.3 +/− 3.1 |

As readily observed from the data the solubilized TCC did not interfere with the enhanced rinsability when utilizing the AEC.

In each of these experiments of Examples 2 and 3, the results are statistically significant.

Therefore as shown by the data, the usage of AECs effectively solubilize carbanilide antibacterial materials, bring about superfatting, and bring about a surprising effect of increased rinsability of the soap from a keratinous surface, even when a carbanilide antibacterial agent is present in the soap.

We claim:

1. A solid composition comprising
   a. an anionic surfactant or mixture thereof, wherein soap is present in quantities of at least 5 wt % of the composition,
   b. an alcohol ethoxycarboxylic acid of the formula $$R\text{—}(OCH_2CH_2)_n\text{—}O\ CH_2\ COOH$$

wherein R is an alkyl of an average of about 8 to 20 carbon atoms inclusive and n is a number of 1 to about 20,
   c. a carbanilide antibacterial agent in antibacterial effective quantities wherein component b is at least about 1 wt. % of the composition.

2. The composition in accordance with claim 1 wherein R is an alkyl of about 10 to about 18 carbon atoms inclusive and n is about 3 to about 12.

3. The composition in accordance with claim 1 wherein the carbanilide is triclocarban.

4. The composition in accordance with claim 3 wherein the triclocarban is from about 0.1 to 1.0 wt. % of the composition.

5. The composition in accordance with claim 4 wherein R is 12 to 15 carbon atoms inclusive and n is about 4 to about 11.

6. A solid composition preparing by mixing
   a. a cleansing effective amount of an anionic surfactant or mixture thereof,
   b. an alcohol ethoxycarboxylic acid of the formula $$R\text{—}(OCH_2CH_2)_n\text{—}O\ CH_2COOH$$

wherein R is an alkyl of an average of about 8 to 20 carbon atoms inclusive and n is a number of 1 to about 20,
   c. a carbanilide antibacterial agent in antibacterial effective quantities wherein component b is in sufficient quantities to solubilize the carbanilide antibacterial agent.

\* \* \* \* \*